United States Patent
Govari et al.

(10) Patent No.: US 10,034,653 B2
(45) Date of Patent: Jul. 31, 2018

(54) TISSUE DEPTH ESTIMATION USING GATED ULTRASOUND AND FORCE MEASUREMENTS

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yaron Ephrath, Karkur (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 278 days.

(21) Appl. No.: 14/992,389

(22) Filed: Jan. 11, 2016

(65) Prior Publication Data
US 2017/0196536 A1    Jul. 13, 2017

(51) Int. Cl.
*A61B 8/08* (2006.01)
*A61B 8/00* (2006.01)
*A61B 8/12* (2006.01)

(52) U.S. Cl.
CPC ............ *A61B 8/0858* (2013.01); *A61B 8/085* (2013.01); *A61B 8/0883* (2013.01); *A61B 8/12* (2013.01); *A61B 8/429* (2013.01); *A61B 8/4405* (2013.01); *A61B 8/485* (2013.01); *A61B 8/5207* (2013.01); *A61B 8/5223* (2013.01)

(58) Field of Classification Search
CPC ......... A61B 8/00; A61B 8/485; A61B 8/0858; A61B 8/085; A61B 8/0883; A61B 8/12; A61B 8/429; A61B 8/4405; A61B 8/5207; A61B 8/5223
See application file for complete search history.

(56) References Cited

U.S. PATENT DOCUMENTS

| 6,226,542 B1 | 5/2001 | Reisfeld |
| 6,301,496 B1 | 10/2001 | Reisfeld |
| 6,814,733 B2 | 11/2004 | Schwartz et al. |

(Continued)

FOREIGN PATENT DOCUMENTS

| JP | 2012 086002 A | 5/2012 |
| WO | 2014/115056 A1 | 7/2014 |
| WO | 2015/113813 A1 | 8/2015 |

OTHER PUBLICATIONS

Bartlett, J. W., and C. Frost. "Reliability, repeatability and reproducibility: analysis of measurement errors in continuous variables." Ultrasound in obstetrics & gynecology 31, No. 4 (2008): 466-475.*

(Continued)

*Primary Examiner* — Carolyn Pehlke
(74) *Attorney, Agent, or Firm* — Notaro, Michalos & Zaccaria P.C.

(57) ABSTRACT

A method for estimating a thickness of tissue includes receiving multiple measurements, each measurement indicating (i) a respective mechanical pressure applied to the tissue, and (ii) one or more round-trip propagation times of an ultrasound wave traversing the tissue in the presence of the respective mechanical pressure. A set of the measurements is selected, having mechanical pressures that fall in a specified partial subrange of mechanical-pressure values. The thickness of the tissue is estimated based on the round-trip propagation times in the selected set of the measurements.

10 Claims, 4 Drawing Sheets

(56) References Cited

U.S. PATENT DOCUMENTS

| | | | |
|---|---|---|---|
| 6,892,091 B1 | 5/2005 | Ben-Haim et al. | |
| 6,997,924 B2 | 2/2006 | Schwartz et al. | |
| 7,156,816 B2 | 1/2007 | Schwartz | |
| 7,536,218 B2 | 5/2009 | Govari et al. | |
| 7,756,576 B2 | 7/2010 | Levin | |
| 8,545,408 B2 | 10/2013 | Sliwa et al. | |
| 8,628,473 B2 | 1/2014 | Sliwa et al. | |
| 2006/0052696 A1* | 3/2006 | Shiina | A61B 5/0048 600/437 |
| 2011/0028848 A1 | 2/2011 | Shaquer et al. | |
| 2011/0144491 A1 | 6/2011 | Sliwa et al. | |
| 2012/0259194 A1 | 10/2012 | Selkee | |
| 2012/0321165 A1* | 12/2012 | Suda | G01S 7/5205 382/131 |
| 2013/0190726 A1* | 7/2013 | Kesner | A61M 25/0105 604/510 |
| 2014/0100563 A1 | 4/2014 | Govari et al. | |
| 2015/0018679 A1 | 1/2015 | Endo | |
| 2016/0183915 A1* | 6/2016 | Govari | A61B 8/429 600/450 |

OTHER PUBLICATIONS

European Search Report, Application No. 17150756.9, dated May 30, 2017.

\* cited by examiner

TISSUE DEPTH ESTIMATION USING GATED ULTRASOUND AND FORCE MEASUREMENTS

FIELD OF THE INVENTION

The present invention relates generally to tissue measurement using ultrasonic waves, and specifically to tissue depth using ultrasonic probe and force Measurements.

BACKGROUND OF THE INVENTION

Ultrasonic techniques are used in catheters for measuring tissue depth. Examples of prior art techniques are provided below.

U.S. Pat. No. 8,628,473, whose disclosure is incorporated herein by reference, describes an ablation catheter with acoustic monitoring that comprises an elongated catheter body. A distal member disposed adjacent a distal end and including an ablation element to ablate a biological member at a target region outside the catheter body. One or more acoustic transducers, each configured to direct an acoustic beam toward a respective target ablation region and receive reflection echoes therefrom.

U.S. Patent application publication 2011/0144491, whose disclosure is incorporated herein by reference, describes a directable acoustic transducer assembly for use in a medical insertion device (MID). In an embodiment, the assembly aims an acoustic signal in response to a sensed or detected force or load imposed on the MID. The directable acoustic transducer assembly includes a switch array and a plurality of directional acoustic transducer elements. The switch array responds to the force or load and activates the directional acoustic transducer elements closest to the source of the force or load. The switch array may include a plurality of switches, at least one of which responses to a force or load and may activate directional acoustic transducer elements having a target tissue in the field of view.

U.S. Patent application publication 2011/0028848, whose disclosure is incorporated herein by reference, describes a device for measuring a spatial location of tissue surface, such as the interface between different types of tissues or between tissue and body fluids. The device includes an elongate catheter body having a distal end portion, a plurality of localization elements carried by the distal end portion, and at least one pulse-echo acoustic element carried by the distal end portion.

U.S. Pat. No. 8,545,408, whose disclosure is incorporated herein by reference, describes an ablation system that comprises a catheter including a pulse-echo ultrasonic transducer disposed in a distal portion and arranged to emit and receive an acoustic beam. The transducer emits and receives acoustic pulses to provide transducer detected information regarding the targeted tissue region being ablated. A rotation mechanism rotates at least the distal portion around a longitudinal axis of the catheter. A control and interface system processes the transducer detected information and provides feedback to a user via a user interface and/or the control and interface system to be used to control ablation.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention that is described herein provides a method for estimating a thickness of tissue. The method includes receiving multiple measurements, each measurement indicating (i) a respective mechanical pressure applied to the tissue, and (ii) one or more round-trip propagation times of an ultrasound wave traversing the tissue in the presence of the respective mechanical pressure. A set of the measurements is selected, having mechanical pressures that fall in a specified partial subrange of mechanical-pressure values, and the thickness of the tissue is estimated based on the round-trip propagation times in the selected set of the measurements.

In some embodiments, selecting the set includes analyzing stability levels of the mechanical-pressure values in two or more subranges of the mechanical-pressure values, and selecting the measurements that fall within the subrange having a best stability level. In other embodiments, the specified partial subrange includes a vicinity of zero mechanical pressure. In yet other embodiments, selecting the set includes determining one or more time periods in which the mechanical-pressure values fall within the selected subrange, and selecting the measurements that were acquired during the time periods.

In an embodiment, estimating the thickness includes filtering-out round-trip propagation times, within the time periods, which fall outside predefined round-trip limits. In another embodiment, estimating the thickness includes analyzing repeatability of the round-trip propagation times among the time periods. In yet another embodiment, receiving the multiple measurements includes receiving measurements of mechanical-pressure that vary from one measurement to another.

There is additionally provided, in accordance with an embodiment of the present invention, a system for estimating a thickness of tissue. The system includes an interface and a processor. The interface is configured to receive multiple measurements, each measurement indicating (i) a respective mechanical pressure applied to the tissue, and (ii) one or more round-trip propagation times of an ultrasound wave traversing the tissue in the presence of the respective mechanical pressure. The processor is configured to select a set of the measurements, having mechanical pressures that fall in a specified partial subrange of mechanical-pressure values, and to estimate the thickness of the tissue based on the round-trip propagation times in the selected set of the measurements.

The present disclosure will be more fully understood from the following detailed description of the embodiments thereof, taken together with the drawings, in which:

DETAILED DESCRIPTION OF EMBODIMENTS

Overview

Figure 1:
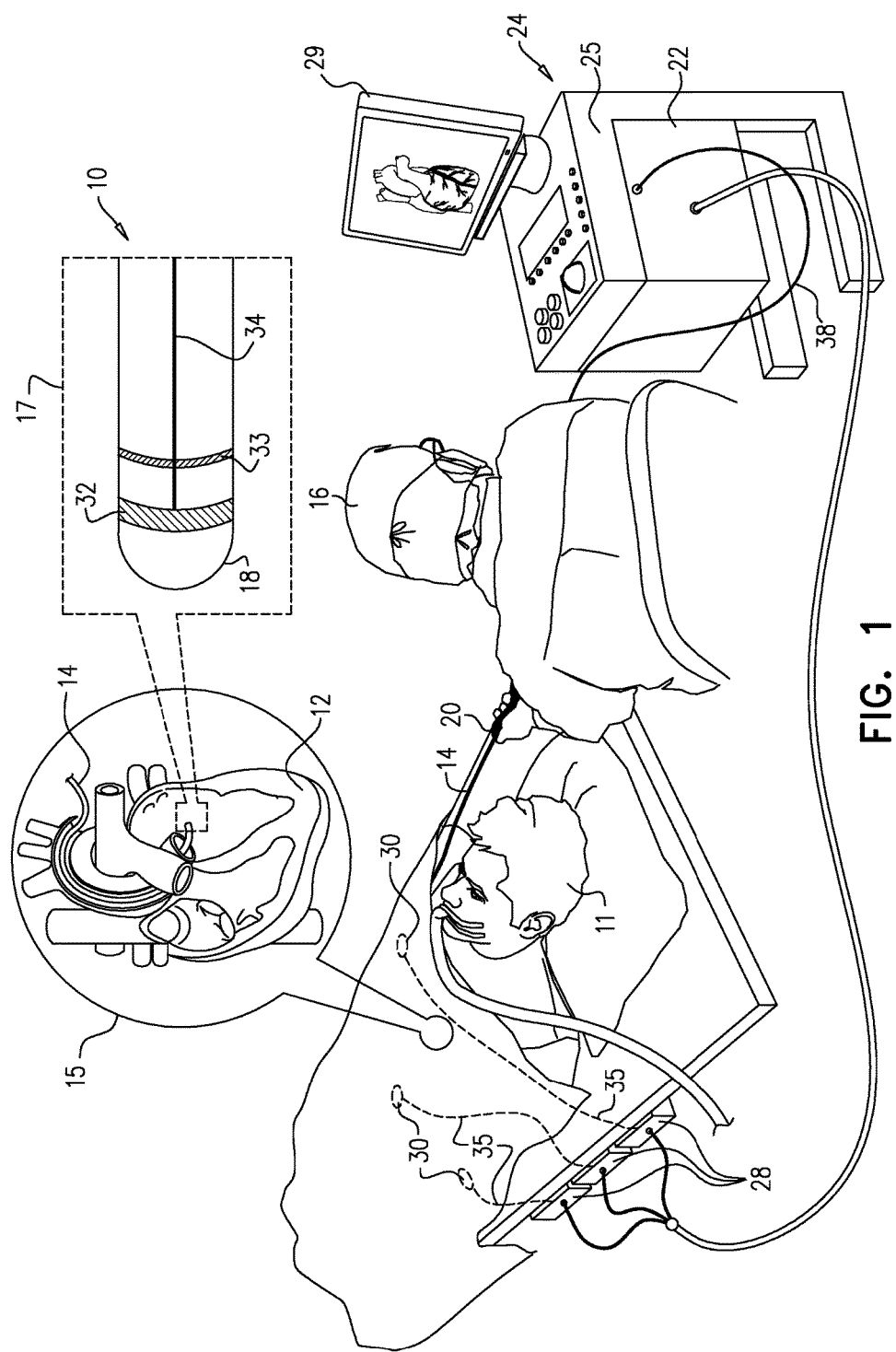
FIG. 1 is a schematic, pictorial illustration of a catheterization system, in accordance with an embodiment of the present invention.

Measurements of tissue depth are used in a variety of therapeutic and diagnostic medical procedures. For example, for accurate ablation, knowledge of the tissue depth is important for setting ablation parameters such as ablation duration and power.

Minimally-invasive measurement techniques, such as ultrasound (US) techniques, may be applied using a catheter. An US transducer is coupled to the tissue in question, transmits US pulses through the tissue and detects echo pulses reflected back from a tissue interface. Time-of-flight (TOF) techniques that measure the propagation delay between sending the US pulses and receiving the echo pulses from an interface in tissue may be used to estimate the depth of the tissue. Since the propagation velocity of ultrasonic pulse is known, the US system can estimate the depth (or thickness) of the tissue in question by concluding the thickness from the measured TOF (divided by 2 for one way propagation delay).

Organs typically comprise multiple tissues that are separated by respective interfaces. Some of the US pulses may propagate through and beyond the tissue in question and be reflected back from the interface of a deeper tissue. Such reflections may interfere with the detection of the pulses reflected form the interface of the tissue in question. The US system has to filter the irrelevant returned pulses, and to base the thickness estimation only on the pulses reflected from the interface of the tissue in question. In addition, the US system has to filter-out TOF values that correspond to out-of-range depth (e.g., 10 cm depth for tissue with expected depth range of 1-2 cm) so as to provide a user (e.g., a physician) with a precise depth estimation of the tissue in question.

Embodiments of the present invention that are described herein provide improved techniques for estimating tissue depth using US and force measurements. In some embodiments, a system for estimating the tissue thickness comprises a mechanical pressure sensor and an US transducer. The sensor is configured to measure mechanical pressure applied to the tissue by the catheter. The pressure typically varies over time, e.g., periodically. The transducer is configured to transmit US pulses through the tissue, in the presence of the respective mechanical pressure, and to receive waves traversing the tissue in question and returning to the transducer.

In some embodiments, the system comprises a processor, which is configured to receive the values of the mechanical pressure and round-trip propagation delays (e.g., TOF) of the US waves reflected from the tissue interface, and to use these measurements for estimating the tissue thickness.

In particular, the inventors have found that the tissue thickness estimation is considerably more stable and reliable if gated by mechanical pressure in a narrow subrange of small-value mechanical pressure values (e.g., a narrow subrange in the vicinity of zero mechanical pressure values). Thus, in some embodiments the processor selects a subrange of the pressure measurements, and uses only the TOF values that fall in this subrange for estimating the thickness of the tissue in question.

In other words, the processor estimates the tissue thickness using only the TOF values that were acquired when the mechanical pressure fell within a selected narrow subrange of pressure values. In some embodiments, the subrange of pressure values may be re-selected adaptively (either manually or automatically by the processor), until stable TOF measurements are obtained.

System Description

FIG. 1 is a schematic, pictorial illustration of a catheterization system 10, in accordance with an embodiment of the present invention. System 10 comprises a catheter 14, which is inserted by a physician 16 through the vascular system of a patient 11 into a chamber or vascular structure of a heart 12, as shown in an inset 15. The physician brings a distal tip 45 of the catheter into contact with the heart wall, for example, at an ablation target site. One commercial product embodying elements of system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluating electrical activation maps, can be ablated by applying thermal energy to the myocardium, e.g., by passing radiofrequency (RF) electrical current through wires in the catheter to one or more electrodes at distal tip 45. Electrical activation maps may be prepared, according to the methods disclosed in U.S. Pat. Nos. 6,226,542, and 6,301,496, and in commonly assigned U.S. Pat. No. 6,892,091, whose disclosures are incorporated herein by reference.

The ablation energy is absorbed in the tissue, heating it to a point (typically above 60° C.) at which the tissue permanently loses its electrical excitability. When successful, this procedure creates non-conducting lesions in the cardiac tissue, which disrupt the abnormal electrical pathway causing the arrhythmia. The principles of the disclosed techniques can be applied to additional areas of the heart so as to diagnose and treat arrhythmia.

Catheter 14 comprises a handle 20, having suitable controls on the handle to enable physician 16 to steer, position and orient the distal end of the catheter as desired for the ablation. Distal tip 45 comprises position sensors (not shown) that convey signals to a processor 22 comprised in a console 24.

Console 24 further comprises one or more ablation power generators 25, which are configured to convey ablation energy and electrical signals to and from heart 12, respectively. Referring to an inset 17, generators 25 convey the ablation energy into heart 12 via a cable 34 and one or more ablation electrodes 32 located at or near distal tip 45. The distal end of catheter 14 further comprises sensing electrodes 33, which are configured to sense electrical signals from heart 12 and convey the signals, via a cable 38, to processor 22.

System 10 further comprises wire connections 35 configured to link console 24 with body surface electrodes 30 and other components of a positioning subsystem for measuring location and orientation coordinates of catheter 14. Electrodes 32 and body surface electrodes 30 may be used to measure tissue impedance at the ablation site as taught in U.S. Pat. No. 7,536,218, issued to Govari et al., which is incorporated herein by reference. In some embodiments, temperature sensor (not shown), typically a thermo-couple or thermistor, is mounted on or near each of the electrodes 32.

Catheter 14 may be adapted to conduct ablative energy to the heart using any known ablation technique, e.g., RF energy, ultrasound energy, and laser-produced light energy. Such methods are disclosed in commonly assigned U.S. Pat. Nos. 6,814,733, 6,997,924, and 7,156,816, which are incorporated herein by reference.

In an embodiment, the positioning subsystem comprises a magnetic position tracking apparatus, which is configured to determine the position and orientation of catheter 14 by generating magnetic fields in a predefined working volume and sensing these fields at the catheter, using field generating coils 28. The positioning subsystem is described, for example, in U.S. Pat. No. 7,756,576, which is incorporated herein by reference, and in the above-noted U.S. Pat. No. 7,536,218.

Processor 22 comprises signal processing circuits (not shown) that typically receive, amplify, filter and digitize signals from catheter 14. Such sensors include, for example, signals generated by sensors such as electrical, temperature and contact force sensors, and a plurality of location sensing electrodes (not shown) located distally in catheter 14. The digitized signals are received by console 24 and the positioning system and used to compute the position and orientation of catheter 14, and to analyze the electrical signals.

In some embodiments, processor 22 further comprises an electro-anatomic map generator, an image registration program, an image or data analysis program and a graphical user interface configured to present graphical information on a display 29.

Processor 22 typically comprises a general-purpose processor, which is programmed in software to carry out the functions described herein. The software may be downloaded to the computer in an electronic form, over a network, for example, or it may, alternatively or additionally, be provided and/or stored on non-transitory tangible media, such as magnetic, optical, or electronic memory.

System 10 typically comprises additional elements, which are not shown in the figures for the sake of simplicity. For example, system 10 may comprise an electrocardiogram (ECG) monitor, coupled to receive signals from one or more body surface electrodes, in order to provide an ECG synchronization signal to console 24. System 10 may further comprise a reference position sensor, either on an externally-applied reference patch attached to the exterior of the subject's body, or on an internally-placed catheter, which is inserted into heart 12 maintained in a fixed position relative to heart 12.

Conventional pumps and lines for circulating liquids through catheter 14 for cooling the ablation site are provided. System 10 may further receive image data from an external imaging modality, such as a magnetic resonance imaging (MRI) unit, and may comprise image processors that can be incorporated in or invoked by the processor 22 for generating and displaying images.

Estimating Thickness of Tissue

Medical procedures may require an estimation of the tissue thickness. In case of minimally invasive procedures, such as tissue ablation, catheter 14 may comprise an ultrasound (US) transducer. During operation, the catheter is brought into contact with the tissue in question. The transducer transmits US pulses that travel through the tissue, as well as through surrounding tissue in the respective organ. Some of the pulses impinge on elements of the organ (e.g., tissue in question and other tissue) and reflect back to the transducer as returned pulses. Thus, some of the returned pulses may return to the transducer from areas in the organ which are not relevant for the estimated thickness of the tissue in question. Using such irrelevant returned pulses in the estimation may cause errors in thickness estimation, and may risk the patient's safety or effectiveness of treatment due to wrong setting of the parameters for ablation of the respective tissue. Techniques that acquire and select only the returned pulses that are relevant for the estimation of the tissue thickness are important for enabling accurate estimation of the tissue in question.

Figure 2:
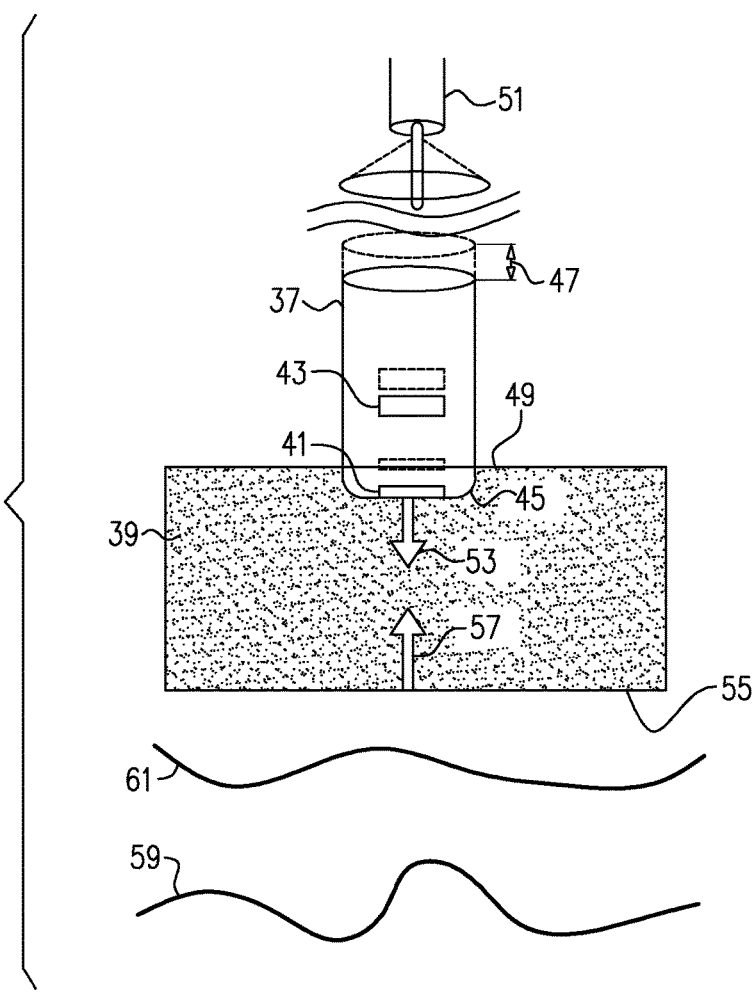
FIG. 2 is a schematic, pictorial illustration of a distal end of a catheter in contact with a tissue being evaluated, in accordance with an embodiment of the present invention.

FIG. 2 is a schematic, pictorial illustration of a distal tip 45 of a catheter 37 in contact with tissue 39 being evaluated, in accordance with an embodiment of the present invention. Catheter 37 can be used for implementing catheter 14 illustrated in FIG. 1, in which case tissue 39 comprises a section of the wall of heart 12. Catheter 37 comprises an ultrasonic transducer 41, which is configured to produce ultrasonic waves traversing tissue 39. Catheter 37 further comprises a contact force sensor 43, disposed at or near distal tip 45.

During heartbeats, a surface 49 of tissue 39 typically shifts up/down in a direction 47 when blood is pumped into/out of the respective cavity of heart 12. In some embodiments, tip 45 remains static and substantially orthogonal to surface 49, so that during heartbeats, force sensor 43 measures a time-cyclic force in response to the heartbeats. When blood is pumped into the respective cavity of heart 12, the cavity expands and sensor 43 measures high force. When blood is pumped out of the cavity, the measured force is close to zero.

In other embodiments, catheter 37 reciprocates in direction 47, thereby compressing and decompressing at least the region of the tissue 39 that is immediately beneath the tip 45. The movement of catheter 37 may occur at frequencies of 1-10 Hz and are performed with sufficient force to compress tissue 39 by 0.3-0.5 mm, and as much as 5 mm. Reciprocation of the catheter 37 may be driven by a mechanical actuator 51.

During operation, transducer 41 produces ultrasound pulses 53 traversing tissue 39 from upper surface 49 toward a lower surface, denoted tissue interface 55, which is the opposite surface of tissue 39. Pulses 53 are reflected as pulses 57 and travel upwards to the surface of tip 45. The round-trip propagation times of the ultrasound pulses traversing the tissue in the presence of the respective mechanical pressure is denoted time-of-flight (TOF). Based on the known speed of ultrasound pulses in the tissue, processor 22 may translate the time-of-flight into a measured depth, or thickness, of tissue 39.

In an embodiment, the practical range of time-of-flight reflections may be bounded according to the cavity in which catheter 37 is located in order to increase the sensitivity of the thickness estimation. For example, the possible range of time-of-flight for a reflection for the right atrium would correspond to tissue thickness of 0.25-7 mm and is considerably less than the full range of the ultrasound transducer or those needed to evaluate the left ventricle. In the left ventricle the possible range of time-of-flight for a reflection would typically correspond to tissue thickness of 2-20 mm.

Suitable sensors for contact force sensor 43 are described, for example, in U.S. Patent Application Publications 2012/0259194 and 2014/0100563, which are incorporated herein by reference.

Transducer 41 may be a known single crystal type that emits ultrasound pulses 53 in a motion mode (M-mode) at a typical rate of 10 MHz. Tissue 39 may be a wall of a heart chamber, and tissue interface 55 the overlying epicardium. The time-of-flight of pulses 53, 57 vary as the tip 45 approaches and recedes from the tissue interface 55.

Other reflections may also be detected by transducer 41. These are exemplified in FIG. 2 by reflective interfaces 59, 61. The variations in the times-of-flight respectively associated with interfaces 59, 61 correlate less well with the measured contact force as well as the motion of catheter 37 than does the time-of-flight associated with interface 55. Interface 55 can be identified among candidate reflections as having a time-of-flight with the highest correlation with the contact force measurements in catheter 37.

Additional aspects of TOF and contact-force measurements, as illustrated in FIGS. 1 and 2, are addressed in U.S. Patent Application Publication 2016/013915, filed Dec. 30, 2014, whose disclosure is incorporated herein by reference.

Figure 3:
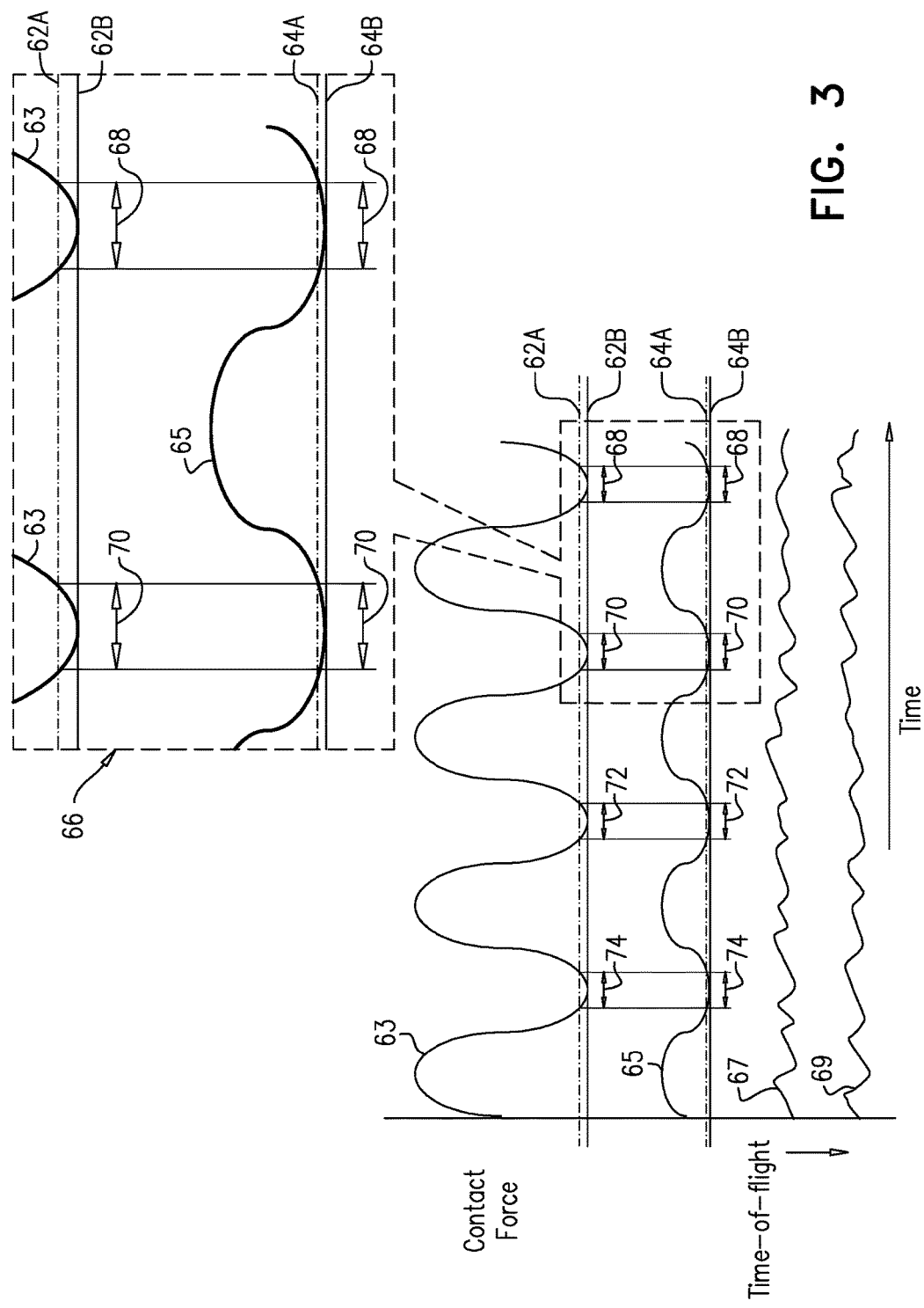
FIG. 3 is a graph showing a correlation between the force applied to a catheter tip and corresponding round-trip propagation times of ultrasound signals reflected from tissue interfaces, in accordance with an embodiment of the present invention.

FIG. 3 is a set of graphs showing a correlation between the mechanical force applied to catheter tip 45 and corresponding round-trip propagation times of ultrasound tracings 65, 67 and 69 reflected from tissue interfaces, in accordance with an embodiment of the present invention. A tracing 63 represents the mechanical pressure (also referred to as contact force) as measured by sensor 43. Tracings 65, 67, 69 represent times-of-flight associated with tissue interfaces 55, 59, and 61 (FIG. 2), respectively. It is evident from inspection that the morphology of tracing 65 correlates well with that of tracing 63, while tracings 67, 69 appear to be uncorrelated with tracing 63.

The correlation may be confirmed by processor 22, for example using a correlation formula such as depicted In U.S. Patent Application Publication 2016/013915, to Govari et al. (filed Dec. 30, 2014), which is incorporated herein by reference. Typically, the computations are applied to the last two seconds of the tracing. However, this interval is not critical. Based on the correlations, it may be concluded from tracing 65 that tissue interface 55 is most likely to correspond to the far wall (i.e., interface 55) of tissue 39.

Referring to an inset 66, in some embodiments, processor 22 sets an upper control limit (UCL) 62A and a lower control limit (LCL) 62B to determine a partial subrange of the force (i.e., mechanical pressure) measurements depicted in tracing 63. Typically, the values and range of the subset are selected so as to provide stable and repetitive readings of force and TOF values. In the example of FIG. 3, tracing 63 is collected over multiple separate time periods, such as periods 68, 70, 72 and 74, in which the force values fall within the partial subrange of the force.

The inventors have found that the tissue thickness estimation is considerably more stable and reliable if gated by mechanical pressure in a narrow subrange, for example in the vicinity of zero mechanical pressure.

In some embodiments, tracing 65 is inspected within periods 68, 70, 72 and 74 in which the time-of-flight (i.e., round-trip propagation time) values are considered stable. In some cases only a subset of the considered stable TOF measurements may be used for estimating the thickness of the tissue.

Additionally, the graph of tracing 65 is repetitive among the selected time periods. For example, only time-of-flight values of tracing 65, within periods 68 and 70, which fall between limits 64A and 64B, are considered sufficiently stable, and can be used to estimate the thickness of tissue 39. On the other hand, any TOF values of tracing 65 within periods 68, 70, 72 and 74 that fall outside limits 64A and 64B are filtered-out and are not used for estimating the thickness of tissue 39.

In yet other embodiments, if a significant portion of time-of-flight values within periods 68, 70, 72 and 74 falls outside limits 64A and 64B, processor 22 updates the values of limits 62A and 62B for selecting a different partial subset of the force measurements.

In an embodiment, the entire set of the TOF measurements may fall in the subrange of the pressure measurements, and may therefore be used for estimating the thickness of the tissue. Typically, however, only a relatively small fraction of the TOF measurements fall in the specified subrange of pressure measurements.

Figure 4:
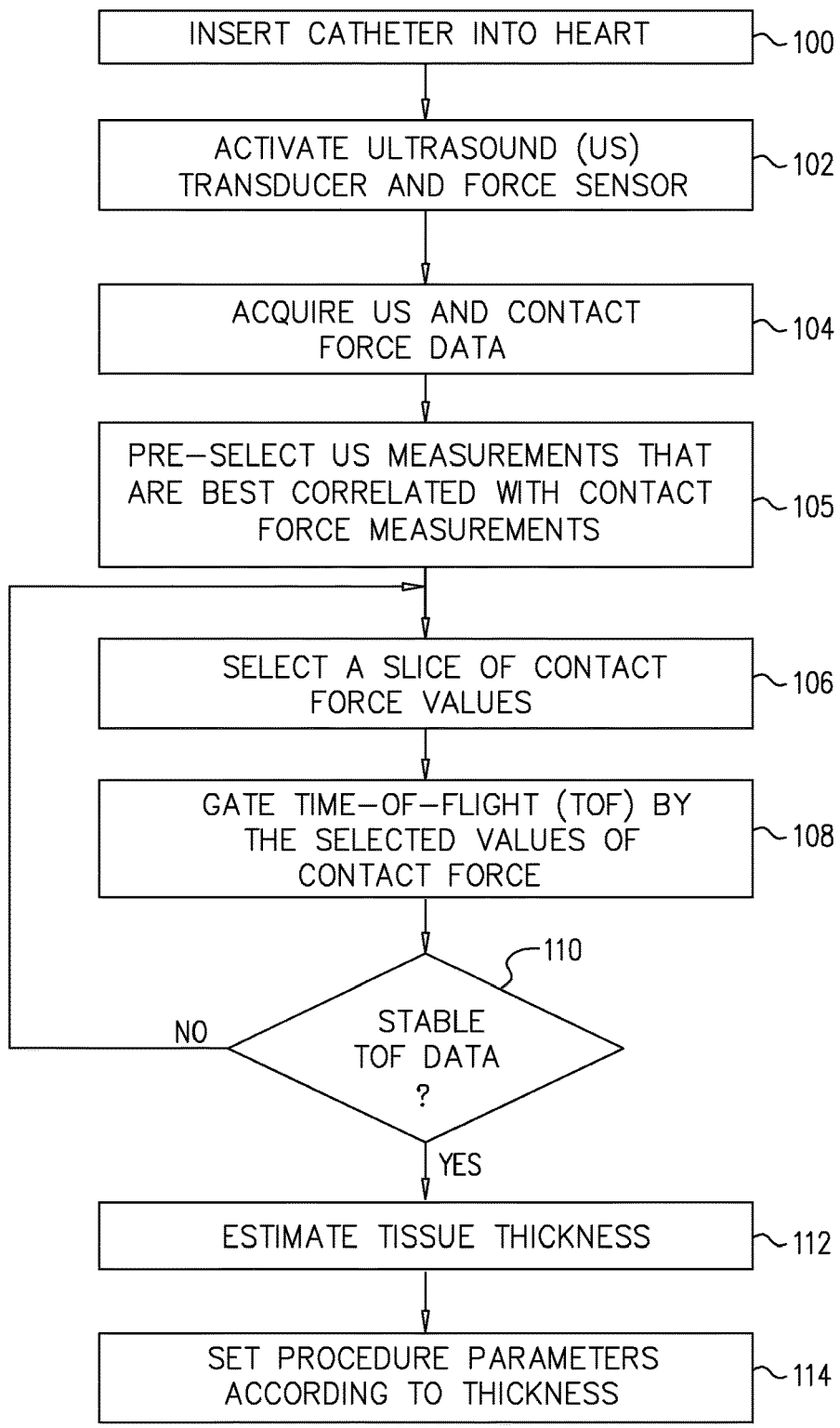
FIG. 4 is a is a flow chart that schematically illustrates a method for determining tissue thickness using ultrasound and force measurements, in accordance with an embodiment of the present invention.

FIG. 4 is a is a flow chart that schematically illustrates a method for determining the thickness of tissue 39 using ultrasound and force measurements, in accordance with an embodiment of the present invention. The method begins with physician 16 inserting the distal end of catheter 14, which incorporates contact force sensor 43 and US transducer 41, into a patient's heart at a catheter insertion step 100.

At an activation step 102, physician 16 navigates catheter 14 so that tip 45 is brought into contact with tissue 39, and activates force sensor 43 and US transducer 41. When activated, transducer 41 sends US pulses through the tissue and receives at least some pulses that are reflected by the tissue interface. At an acquisition step 104, catheter 14 acquires contact force measurements from sensor 43 and time-of-flight measurements corresponding to the reflected pulses that were received by transducer 41, and conveys the signals, via cable 38, to processor 22.

At a correlation step 105, processor 22 pre-selects the time-of-flight measurements that are best correlated to the contact force measurements. For example, with reference to FIG. 3 above, processor 22 may choose the time-of-flight measurements of tracing 65, which are reflected from tissue interface 55. The time-of-flight measurements of tracings 67 and 69, which are reflected from tissue interfaces 61 and 59, respectively, are discarded.

At a slice selection step 106, in an embodiment, physician 16 specifies a subrange (also referred to as slice) of the force values, which comprises a partial subset of the force measurements. In an alternative embodiment, processor 22 analyzes the acquired force values and automatically specifies the respective subrange, such as the range between limits 62A and 62B.

At a time-of-flight selection step 108, processor 22 selects time periods (e.g., periods 68, 70, 72 and 74) in which the measured force values fall within the specified subrange, e.g., between limits 62A and 62B. Processor 22 selects the corresponding time-of-flight values and analyzes the repeatability and stability levels of the TOF values across one or more periods (e.g., periods 68, 70, 72 and 74).

At a decision step 110, processor 22 checks whether the selected TOF values are sufficiently stable and repeatable for deriving a precise estimation of the thickness of tissue 39. In an embodiment, processor 22 may compare the statistical distribution of the TOF values in two or more time periods (e.g., between periods 68 and 70) for assessing the repeatability level of the TOF values. In another embodiment, processor 22 may use the entire set of TOF values that fall in the subrange of the pressure measurements for estimating the thickness of tissue 39.

In yet another embodiment, processor 22 sets limits 64A and 64B and checks whether any of the selected TOF values falls outside limits 64A and 64B.

In some embodiments, when processor 22 detects that the TOF values in the time periods are not sufficiently stable, the method loops back to slice selection step 106 for selecting a different slice. In other embodiments, processor 22 may filter out TOF values that fall outside limits 64A and 64B and use the remaining TOF values for estimating the tissue depth. The filtered values typically comprise an insignificant portion (e.g., less than a given fraction) of the TOF values within the time periods that fall outside limits 64A and 64B.

In some cases, a significant portion (e.g., most) of the measurements corresponding to one or more time periods (e.g., period 70) may comprise abnormal data, for example, when transducer 41 is temporarily positioned non-orthogonally to surface 49. In yet other embodiments, processor 22 may present an analysis of these abnormal values on screen 29, possibly along with a query to physician 16 of whether to filter-out the abnormal values or to take another action, such as selecting a different slice at step 106.

In case the processor determines that TOF values in the time periods are sufficiently stable, the processor uses the respective TOF values to estimate the thickness of tissue 39, and presents the estimated thickness result on display 29, at a tissue thickness estimation step 112. At a parameter setting step 114, physician 16 uses the estimated thickness for setting one or more parameters that are required for the medical procedure (e.g., ablation parameters). In case physician 16 is unsatisfied with the estimated thickness he or she may return to acquisition step 104, for example, by repositioning the catheter with respect to tissue 39. In another embodiment, the physician may return to slice selection step 106 so as to select another slice by updating limits 62A and 62B.

FIGS. 1-4 show, by way of example, a system and procedures for estimating depth or thickness of tissue 39 comprised in heart 12. The techniques described herein, however, can be used in any other organ of patient 11 using minimally-invasive apparatus or in any other suitable medical procedure or technique involving estimating the depth or thickness of a tissue.

In addition, the time periods selection criteria and filtering techniques applied to the TOF values described herein are given by way of example and other suitable techniques can also be used. The signal acquisition technique described above is not limited to ultrasound procedures and may comprise any suitable technique associated with close proximity or direct contact of the catheter with the tissue in question.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for estimating a thickness of heart wall tissue, the method comprising:
providing a catheter having a distal tip, the catheter comprising:
an ultrasonic transducer, the ultrasonic transducer adapted to produce ultrasound waves which traverse the heart wall tissue,
and a contact force sensor proximate the distal tip;
providing a mechanical actuator associated with the catheter;
driving the catheter in a reciprocating motion in a direction of the heart wall tissue using the mechanical actuator, wherein the reciprocating motion of the catheter periodically compresses the heart wall tissue in a region of the heart wall tissue in proximity to the distal tip;
receiving a plurality of measurements corresponding to the periodic compression, each measurement indicating (i) a respective mechanical pressure applied to the heart wall tissue, and (ii) one or more round-trip propagation times of an ultrasound wave traversing the heart wall tissue in the presence of the respective mechanical pressure;
selecting a set of the measurements, having mechanical pressures that fall in at least one specified partial sub-range of mechanical-pressure values;
and estimating the thickness of the heart wall tissue based on the round-trip propagation times of the selected set of the measurements,
wherein selecting the set comprises determining one or more time periods in which the mechanical-pressure values fall within the at least one selected partial sub-range, and selecting the measurements that were acquired during the one or more time periods, and
wherein estimating the thickness comprises analyzing repeatability of the round-trip propagation times of the selected measurements among the one or more time periods.

2. The method according to claim 1, wherein selecting the set further comprises analyzing stability levels of the mechanical-pressure values in two or more selected partial sub-ranges of the mechanical-pressure values, and selecting the measurements that fall within a selected partial sub-range of the two or more selected partial sub-ranges having a best stability level.

3. The method according to claim 1, wherein the specified partial sub-range comprises an upper and lower limit encompassing zero.

4. The method according to claim 1, wherein estimating the thickness further comprises filtering-out round-trip propagation times of the selected measurements, within the one or more time periods, which fall outside predefined round-trip limits.

5. The method according to claim 1, wherein receiving the plurality of measurements comprises receiving measurements of mechanical pressure that vary from one measurement to another.

6. A system for estimating a thickness of heart wall tissue, comprising:
a catheter comprising:
a distal tip,
an ultrasonic transducer, the ultrasonic transducer adapted to produce ultrasound waves which traverse the heart wall tissue,
and a contact force sensor proximate the distal tip;
a mechanical actuator associated with the catheter, the actuator configured to drive the catheter in a reciprocating motion in a direction of the heart wall tissue, wherein the reciprocating motion of the catheter periodically compresses the heart wall tissue in a region of the heart wall tissue in proximity to the distal tip;
an interface configured to receive a plurality of measurements corresponding to the periodic compression, each measurement indicating (i) a respective mechanical pressure applied to heart wall the tissue, and (ii) one or more round-trip propagation times of an ultrasound wave traversing the heart wall tissue in the presence of the respective mechanical pressure;

and a processor, which is configured to select a set of the measurements, having mechanical pressures that fall in at least one specified partial sub-range of mechanical-pressure values, and to estimate the thickness of the heart wall tissue based on the round-trip propagation times of the selected set of the measurements, wherein the processor is configured to determine one or more time periods in which the mechanical-pressure values fall within the at least one specified partial sub-range, and to analyze the measurements that were acquired during the one or more time periods, and wherein the processor is configured to analyze repeatability of round-trip propagation times of the selected measurements among the one or more time periods.

7. The system according to claim 6, wherein the processor is configured to analyze a stability level of the mechanical-pressure values in two or more selected partial sub-ranges of the mechanical-pressure values, and selecting the measurements that fall within a selected partial sub-range of the two or more selected partial sub-ranges having a best stability level.

8. The system according to claim 6, wherein the specified partial sub-range comprises an upper and lower limit encompassing zero.

9. The system according to claim 6, wherein the processor is configured to filter-out round-trip propagation times of the selected measurements, within the one or more time periods, which fall outside predefined round-trip limits.

10. The system according to claim 6, wherein the interface is configured to receive measurements of mechanical pressure that vary from one measurement to another.

* * * * *